US005446934A

United States Patent [19]

Frazier

[11] Patent Number: 5,446,934

[45] Date of Patent: Sep. 5, 1995

[54] BABY MONITORING APPARATUS

[76] Inventor: Richard K. Frazier, 501 Slater's La., Suite 914, Alexandria, Va. 22314

[21] Appl. No.: 159,364

[22] Filed: Nov. 30, 1993

[51] Int. Cl.[6] .................. A61G 11/00; A47D 7/00; A61M 23/00

[52] U.S. Cl. .................. 5/655; 5/97; 5/421; 5/904; 5/658; 5/915; 600/22; 601/47; 601/48; 601/111

[58] Field of Search .................. 5/97, 93.1, 421, 655, 5/915, 904, 658, 414, 109; 600/22; 601/47, 48, 111

[56] References Cited

U.S. PATENT DOCUMENTS

| | | | |
|---|---|---|---|
| 1,420,134 | 6/1922 | Nisle . | |
| 1,688,200 | 10/1928 | Morgentmaler | 5/421 |
| 2,559,654 | 7/1951 | Netteland | 5/97 |
| 3,292,611 | 12/1966 | Belkin | 5/904 |
| 3,858,570 | 1/1975 | Beld et al. | 600/22 |
| 3,878,570 | 4/1975 | Donnelly | 5/97 |
| 3,921,233 | 11/1975 | Mann | 5/97 |
| 3,993,042 | 11/1976 | Gatts | 5/904 |
| 4,129,123 | 12/1978 | Smidak | 128/1 |
| 4,628,553 | 12/1986 | Buttitta et al. | 5/655 |
| 4,671,284 | 6/1987 | Wilson et al. | 5/915 |
| 4,779,615 | 10/1988 | Frazier | 601/111 |
| 4,785,797 | 11/1988 | Cuervo | 5/915 |
| 4,947,832 | 8/1990 | Blitzer | 5/109 |
| 4,989,600 | 2/1991 | Collier | 128/372 |
| 5,003,651 | 4/1991 | Rosen | 5/109 |
| 5,006,105 | 4/1991 | Sherard | 600/22 |
| 5,054,138 | 10/1991 | Wesley | 5/93 |
| 5,081,722 | 1/1992 | Yu | 5/99 |
| 5,088,138 | 2/1992 | Munster | 5/109 |
| 5,183,457 | 2/1993 | Gatts et al. | 5/655 |
| 5,330,415 | 7/1994 | Storti et al. | 600/22 |

*Primary Examiner*—Alexander Grosz

*Attorney, Agent, or Firm*—Roland P. Kananen

[57] ABSTRACT

A baby holding pen or crib includes automatic position adjusting, monitoring, and interactive communication means, including alarms, for communicating information to and from the crib or pen from a remote location. Such means include interactive audio and visual means, such as prerecorded messages and preprogrammed tactile simulation. The crib includes a combination of a bed surface that is adjustable in both longitudinal and lateral angles; a heating an cooling means to maintain the crib area at a comfortable temperature; speakers that play back prerecorded sounds to the baby such as a recording of a mother's soothing voice or instructions to attendants to the location of the crib; visual sensing equipment, such as video monitors, including alarms to remind an attendant of feeding time, diaper changing time, bathing time, or medicine dosage time; and a plurality of sensors, including temperature sensors, vital function sensors, and the like.

9 Claims, 2 Drawing Sheets

BABY MONITORING APPARATUS

BACKGROUND OF THE INVENTION

The present invention relates to an apparatus for holding and monitoring a baby and, more particularly, to an apparatus for holding a baby and monitoring various conditions of the baby and of the environment surrounding the baby. Still more particularly, this invention relates to such an apparatus in the form of a bed having a closed environment with a plurality of sensors, adjustments, and interactive components for relating instructions to persons attending the infant. Still more particularly, this invention relates to such an apparatus having programmed voice instructions for soothing the baby with the voice of a familiar attendant and for instructing interim attendants according to a prescribed schedule for the baby.

BRIEF DESCRIPTION OF THE PRIOR ART

A number of devices have been developed for monitoring the condition of a baby in a hospital care environment. Among such devices, perhaps the best known for distressed care is an incubator which carefully monitors the condition of the infant in the incubator while carefully controlling temperature and humidity. A number of designs for such hospital care facilities are known to the art, but few if any are available for home utilization in non-distressed conditions.

Similarly, for home use, there are a number of crib and baby devices having a wide variety of designs. Normally, however, such devices are not well automated, usually requiring manual adjustment of the bed surfaces for the child, with little or no attention being given to temperature control for heating or cooling the baby separately from the environmental conditions of the room in which the crib is located.

While sophisticated communication systems are available for transmitting and receiving sound and pictures through suitable recording and reproductions media, baby cribs, whether open or closed, have not traditionally been provided with such monitoring devices for observing or listening to the baby from remote locations, or for providing recordings to the crib. Moreover, such cribs have not been provided with interactive devices for interchanging information with an attendant through video or audio systems providing information on diaper changing time, bathing time, feeding time, or the like. Still further, such devices have not included sensors for such purposes, or for tactilely stimulating or soothing the infant while in the crib.

The Yu U.S. Pat. No. 5,081,722 shows a baby crib with floor members 20 and 30, as seen in FIG. 3, that are adjustable to a desired angle of inclination, a control box 32, external audio equipment, microphones, humidity sensors, and a micro-vibrator, as a representative patent illustrating the state of the combined art.

It is thus an overall purpose of this invention to provide a baby holding and monitoring apparatus having a plurality of such features.

SUMMARY OF THE INVENTION

According to the present invention, a baby holding pen or crib includes automatic position adjusting, monitoring, and interactive communication means, including alarms, for communicating information to and from the crib or pen from a remote location. Such means include interactive audio and visual means, such as prerecorded messages and preprogrammed tactile stimulation.

The crib includes a combination of a bed surface that is adjustable in both longitudinal and lateral angles; a heating and cooling means to maintain the crib area at a comfortable temperature; speakers that play back prerecorded sounds to the baby such as a recording of a mother's soothing voice or instructions to attendants to the location of the crib; visual sensing equipment, such as video monitors, including alarms to remind an attendant of feeding time, diaper changing time, bathing time, or medicine dosage time; and a plurality of sensors, including temperature sensors, vital function sensors, and the like.

By the present invention, a baby holding and monitoring apparatus is provided which includes a bed having a supporting surface adjustable as to angle and firmness for providing the optimum support for the baby. The bed may include a multiple sectional bed, each section being operable with a hydraulic ram to perform the adjustment according to proximate or remote controls. A transparent cover is provided which is either openable or removable by using a withdrawing mechanism and which, with the supporting surface, defines a chamber which provides optimum conditions of heat, air, sound and light. Suitable sensors are provided for monitoring these and other parameters of interest. Preferably, the cover opens in its entirety.

The bed is adjustable from firm to soft, and the angle of the bed is adjustable so that the baby's head can be up or down relative to the rest of its body. The bed can also be tilted to one side or the other to provide optimum orientation of the sleeping surface for the infant. The apparatus includes programmed voice commands prerecorded by, for example, the mother for instructing a person monitoring the baby to feed the baby, change its diaper, administer medicine, and so forth. For hospital use, the voice commands can be programmed by a doctor to include his instructions for the attendants of the baby, thus to avoid human error in interpreting the instructions. In addition to or instead of being instructed by a voice command, the attendants can be instructed by a video screen or by a printout from a suitable ROM (read only memory) of the prerecorded commands. The commands may be recorded on any suitable recording medium such as a floppy or firm disk or diskette, CD disks, and the like. A plurality of baby monitoring apparatuses according to the present invention can be employed to monitor a number of babies, and thereby simplify the tasks of the attendants of determining what each baby needs and when. The apparatus can also assure that the needs of each baby are satisfied. Independent tactile devices are incorporated in the bed to provide the baby with physical contact ranging from gentle touches and reassuring pats to strokes and full body stimulation. One suitable mechanism for providing such stimulation according to a prerecorded prescription is shown in the applicant's prior issued U.S. Pat. No. 4,779,615 which is hereby incorporated by reference.

Specifically, the mechanism for providing tactile stimulation may comprise a plurality of switches in a spaced array, each of the switches having an extendable portion which, when actuated, extends and moved a portion of the supporting surface against a portion of the baby. The tactile stimulating mechanism includes a system for actuating the switches in a sequence according to a prerecorded program.

One or more microphones open to the interior of the chamber permit audible monitoring of the baby both immediately outside of the chamber by the provision of speakers on the exterior of the baby monitoring apparatus and at remote locations by virtue of a transmitter on the apparatus and associated remote receivers. The receivers have displays relating the locations of the speakers to the baby. In addition, video monitors can be provided to the chamber for constantly monitoring the condition of the baby from a remote location, where a plurality of babies could be monitored.

Through the use of a single remote receiving apparatus which is assigned to one person, the responsibility for tending the baby is clearly assigned to the person having possession of the remote audio and video receiver. The possession of the single remote receiver provides a link from one baby attendant to the following baby attendant so that there is clearly always someone in charge of tending the baby.

Detectors can be provided to sense and report the body temperature of the baby. The baby can be provided with emergency food and water.

The cover protects the baby from animals and other small children, and can be drawn closed when strangers are around. Sensors can be provided to monitor body temperatures, and other vital functions can be provided. For example, moisture sensors could be provided to sense bed wetting and other parameters can be non-invasively tested. A video camera can be provided for remotely viewing the baby. Security companies can provide a monitoring service to provide warning to the family of the baby if trouble is detected by any of the sensors of the apparatus.

Comfort programs containing a number of tested and prerecorded commands can be stored in interactive recording media so that they can be activated when necessary to comfort or quiet the baby. Prerecorded programs of music and/or stories can be created and played to help pacify and entertain the baby.

Speakers positioned to be heard within the chamber provide the baby with soothing voice and sound messages. Such messages can come from the recorded voice of the mother for playback when the mother is not home or when a need for soothing words for the baby is detected.

The apparatus can be a family security system, providing protection against intruders and fire to suitable alarms, and warning the family of a sudden temperature change around the baby.

Fire extinguisher and battery-powered emergency lighting are included in the apparatus to protect the baby, the entire family, and the house. The baby monitoring apparatus can act as a family emergency station, a place where the family goes in an emergency, first to check the baby and then to employ all the emergency crisis managing tools which the baby monitoring apparatus places at their fingertips. A first aid kit, which includes supplies for the entire family, can be positioned on the baby monitoring apparatus. The apparatus can also provide emergency outside communication for the family. Although the monitoring apparatus as described herein takes the form of a crib or baby bed, the apparatus can also be used as a playpen.

DETAILED DESCRIPTION OF THE PREFERRED EMBODIMENTS

Figure 1:
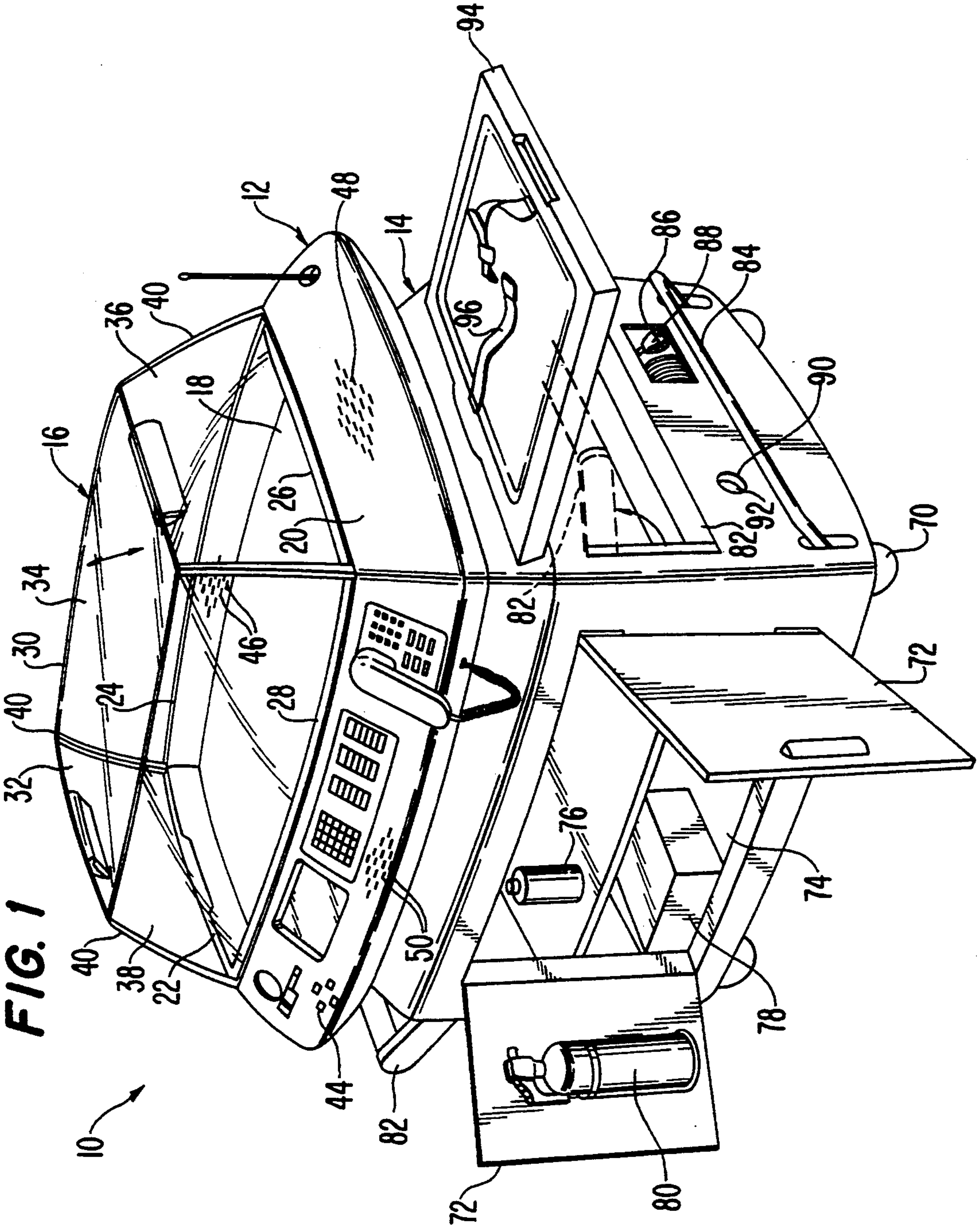
FIG. 1 is perspective view of the baby monitoring apparatus according to the invention, with the cover in place, a slide-out changing table extended, and various compartments opened.

As can be seen from FIG. 1, the baby monitoring apparatus according to the present invention, which is designated generally by the reference numeral 10, includes a first component defining a baby bed 12, a second component defining a movable support or cart 14 for the bed 12, and a third component defining a cover 16 for the bed 12. The bed includes a supporting surface 18 for the baby positioned within a frame 20 and recessed below the top of the frame 20 to define sides 22, 24, 26 and 28 around the supporting surface 18.

The cover 16 includes a plurality of panels of transparent material, such as glass, including a top panel 30 and side panels 32, 34, 36 and 38. The side panels 32–38 define windows which can be opened and closed by sliding on corner posts 40 and into slots (not shown) defined in the frame 20. A power driving mechanism for opening and closing the windows, which can be conventional, is positioned inside the frame 20 and operated by the controls 44 on the frame 20.

A pattern of openings 46 is formed in at least one side 24 of the frame 20 to allow sound to pass to a microphone and speaker (not shown) positioned in the crib, patterns of openings 46 and 50 are positioned on an exterior surface of the frame 20, and a speaker and microphone can be positioned behind each pattern. By this arrangement, the baby can clearly hear the sound of voices outside the chamber defined by the bed 12 and the cover 16 and, at the same time, the baby can be heard outside the chamber.

The cart 14 is supported on roller-ball type casters 70 and defines one or more internal compartments which can be accessed by various doors or covers. Pivoting doors 72 are positioned at an opening 74 which defines a storage area for first aid supplies 76 (represented in FIG. 1 by a bottle), a backup power supply, in the form of, for example, a nickel-cadmium battery pack 78, and a fire extinguisher 80, which can be mounted on the interior side of one of the doors 72.

A swinging handle 82 is positioned at each end of the cart 14, each handle 82 being pivotable from a stored position in which the handle is recessed in the cart 14, as shown at the right end in FIG. 1, and a locked, actuated position, in which the handle extends outward from the end of the cart 14 as is shown at the left end and by the dashed lines at the right end in FIG. 1. A foot-operated lock bar 84 is positioned at at least one of the ends of the cart 14 to lock the casters 70 through an up/down movement of the lock bar 84. An access opening 86 is provided in the cart 14 to permit access to a cord 88 which provides a direct power supply to the baby monitoring apparatus 10, bypassing the battery pack 78. Another access opening 90 is provided in the cart 14 to provide access to a three-prong plug 92.

A changing table 94 slides out of the cart 14 at one end, so as to be cantilevered from the cart in the extended position of the changing table. A safety strap 96 is provided on the changing table 94.

Figure 2:
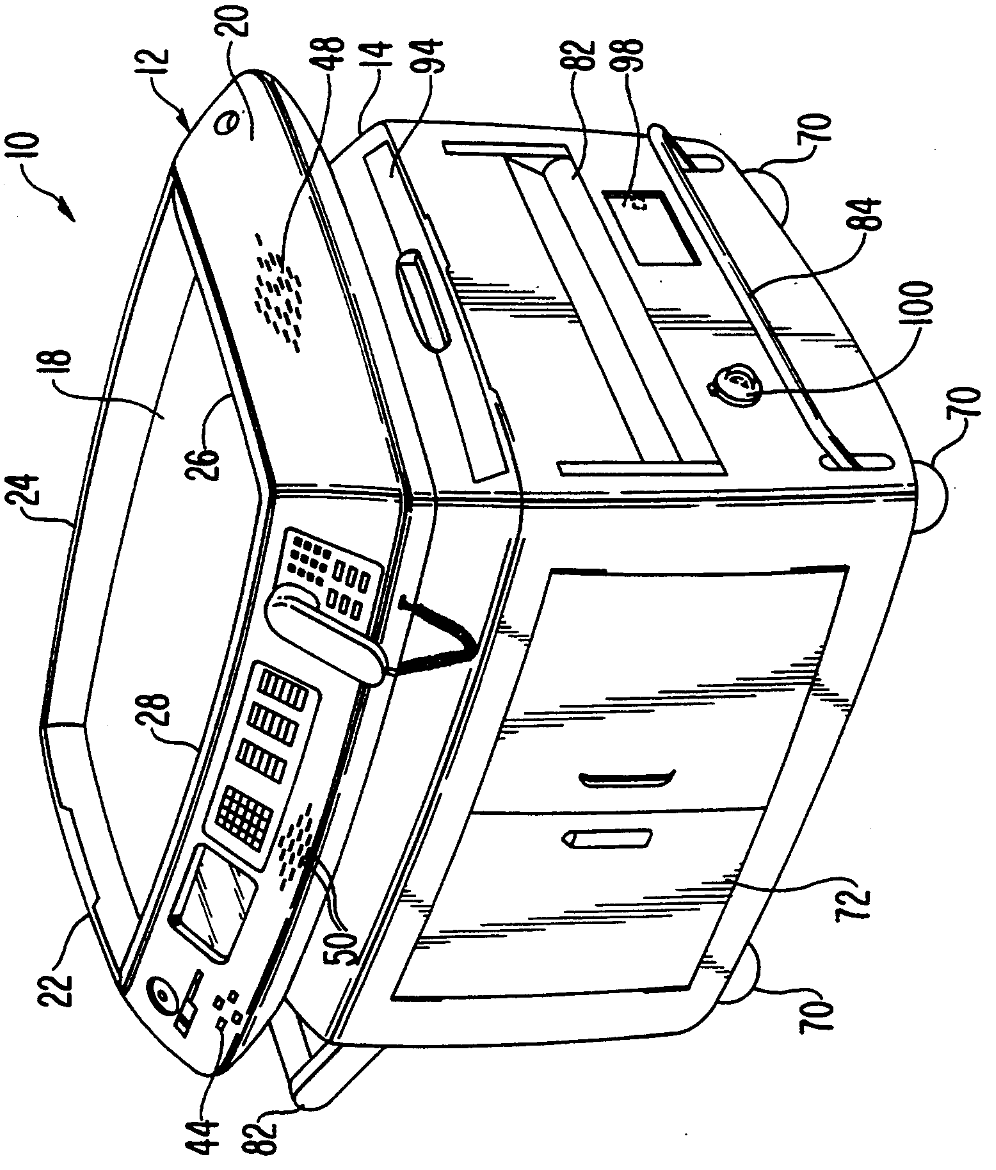
FIG. 2 is a perspective view of the baby apparatus of FIG. 1 with the cover removed and various compartments and features in a closed and/or stored position.

FIG. 2 shows the baby monitoring apparatus according to the present invention in a condition in which the cover 16 is removed from the bed 12. In addition, the antenna is retracted, and the pivoting doors 72 are closed. Furthermore, a sliding door 98 is in a position covering the access opening 86, and a pivoting cover 100 is in a position covering the access opening 90 leading to the grounded hookup 92 for recharging the nickel-cadmium battery pack.

It will be apparent to those skilled in the art and it is contemplated that variations and/or changes in the embodiments illustrated and described herein made be made without departure from the present invention. Accordingly, it is intended that the foregoing description is illustrative only, not limiting, and that the true spirit and scope of the present invention will be determined by the appended claims.

What is claimed:

1. A baby monitoring apparatus, comprising:
- a supporting surface for the baby;
- a cover positioned over the supporting surface and defining an enclosure with the supporting surface;
- means for adjusting the position of the supporting surface;
- means for providing an optimum temperature within the enclosure; and
- means for tactilely stimulating the baby according to a prerecorded program, said means for tactilely stimulating including a plurality of switches in a spaced array, each of said switches having an extendable portion which, when actuated, extends and moves a portion of said supporting surface against a portion of said baby, and means for actuating said switches in a sequence according to said prerecorded program.

2. The apparatus as set forth in claim 1 wherein said position adjusting means further includes means for adjusting said supporting surface in both longitudinal and lateral angles.

3. The apparatus as set forth in claim 1, further including audio means for reproducing prerecorded sounds at the apparatus site.

4. The apparatus as set forth in claim 3, wherein said prerecorded sounds include one or more of instructions for attending to the baby, a familiar voice, or soothing sounds for the comfort of the baby.

5. The apparatus as set forth in claim 1 further including video means for visually monitoring the condition of the baby from a remote location.

6. The apparatus as set forth in claim 1 further including remote control units for interactive communication with said apparatus.

7. A baby monitoring apparatus, comprising:
- an adjustable supporting surface for a baby;
- a cover positioned over the supporting surface and defining an enclosure with the supporting surface;
- a cart supported by wheels, said crib being supported by said cart for easy maneuverability;
- a changing table supported on said cart, said changing table having a retracted storage position and an extended cantilevered position, said table being slidable between said retracted and extended positions;
- a swinging handle positioned at each end of the cart, each handle being pivotable between a first position in which the handle is recessed in the cart for storage and a second position in which the handle extends outward from a respective end of the cart to facilitate maneuvering of the apparatus;
- a foot-operated lock bar positioned adjacent at least one end of the cart to lock the wheels of the cart in a stationary position;
- an internal storage compartment located in said cart for storing baby supplies and emergency equipment;
- means for providing an optimum temperature within the enclosure; and
- emergency equipment disposed within said internal storage compartment of said cart, said emergency equipment including at least a fire extinguisher and a first aid kit.

8. The monitoring apparatus of claim 7, further comprising a means for tactilely stimulating the baby according to a prerecorded program, said means for tactilely stimulating including a plurality of switches in a spaced array, each of said switches having an extendable portion which, when actuated, extends and moves a portion of said supporting surface against a portion of said baby, and means for actuating said switches in a sequence according to said prerecorded program.

9. The monitoring apparatus of claim 7, wherein said emergency equipment further includes a battery-powered emergency light source, and a means for outside communication.

* * * * *